United States Patent [19]

Scott

[11] 3,959,200

[45] May 25, 1976

[54] COPOLYESTER COMPOSITION
[75] Inventor: Paul Thigpen Scott, Kinston, N.C.
[73] Assignee: E. I. Du Pont de Nemours and Company, Wilmington, Del.
[22] Filed: Oct. 25, 1973
[21] Appl. No.: 409,596

[52] U.S. Cl. .................... 260/29.1 SB; 260/75 R; 260/857 PE; 260/860; 128/151; 128/152
[51] Int. Cl.$^2$ .................. A61F 11/00; C08K 5/54; C08L 67/02; C08L 77/00
[58] Field of Search........ 260/75 R, 75 SB, 29.1 SB, 260/40 R, 857 PE, 860; 128/151, 152

[56] References Cited
UNITED STATES PATENTS

| 2,475,802 | 7/1949 | Osserman | 260/17 |
| 2,623,033 | 12/1952 | Snyder | 260/75 R |
| 2,623,034 | 12/1952 | Flory et al. | 260/75 R |
| 2,839,492 | 6/1958 | Caldwell et al. | 260/75 R |
| 2,910,980 | 11/1959 | Stewart | 128/152 |
| 3,097,059 | 7/1963 | Hoffman | 264/155 |
| 3,153,005 | 10/1964 | Minter | 260/40 R |
| 3,491,048 | 1/1970 | Sargent | 260/29.1 SB |
| 3,624,041 | 11/1971 | Brandrup et al. | 260/75 R |
| 3,668,277 | 6/1972 | Riemhofer et al. | 260/75 R |
| 3,779,993 | 12/1973 | Kibler et a. | 260/40 R |

FOREIGN PATENTS OR APPLICATIONS 644,287  10/1950  United Kingdom ............ 260/75 SB

OTHER PUBLICATIONS

Dow Corning Silicone Notebook, Reference No. 2003, Issued June 1952, pp. 2 & 4.

Primary Examiner—Allan Lieberman

[57] ABSTRACT

Disclosed herein is a linear, essentially non-crystalline copolyester composition comprising in polymerized form polymethylene glycol units of 2 to 6 carbon atoms, aliphatic dicarboxylic acid units of 5 to 10 carbon atoms, and isophthalic acid units, the isophthalic acid units comprising from about 10 to 50 mol percent of the total acid units, and the copolyester composition having an intrinsic viscosity in the range of about 0.3 to 0.8. The composition is useful in fabricating custom-molded earplugs by inserting into and sealing the auditory canal of the ear.

8 Claims, No Drawings

COPOLYESTER COMPOSITION

BACKGROUND OF THE INVENTION

This invention relates to novel copolyester compositions that have a very low crystalline habit, such particular copolyesters being especially useful as earplugs. The compositions are pliable at ambient temperatures for easy fabricability of custom-molded earplugs. The custom-molded earplugs fit well, provide good sound attenuation, are comfortable and safe to wear, are easily removable and inexpensive, all qualities that the art teaches are important factors in earplug selection.

SUMMARY OF THE INVENTION

This invention concerns a composition useful in fabricating earplugs. The composition is a linear copolyester comprising in polymerized form
  i. at least one polymethylene glycol of the formula HO—$(CH_2)n$—OH wherein $n$ is an integer of 2 to 6,
  ii. at least one aliphatic dicarboxylic acid of the formula HOOC—$(CH_2)_x$—COOH wherein $x$ is an integer of 3 to 8, and
  iii. isophthalic acid
the isophthalic acid being about 10 to 50 mol percent of the total amount of acid
    the copolyester composition further characterized by having an intrinsic viscosity of about 0.3 to 0.8 and a degree of crystallinity less than about 10% as determined by X-ray diffraction.

This invention also concerns a method for protecting the human ear from excessive sound. The method comprises attenuating sound by inserting into and sealing the auditory canal of the ear with the particular copolyester composition described herein.

A preferred copolyester composition of the present invention is poly(ethylene isophthalate/adipate) wherein the polymethylene glycol used is ethylene glycol, isophthalic acid comprises from 20 to 30 mol percent and adipic acid comprises 70 to 80 mol percent of the acid components.

It has been found that small amounts of silicone oil, not to exceed about one percent of total composition weight, and small amounts of fibers not to exceed about one percent of total composition weight, are helpful if it is desired to decrease tackiness or flowability, respectively, of the novel compositions. Concerning fibers that decrease flowability and stiffen the composition, such fibers can be made from various materials including nylon and polyester.

Fibers should generally be between about ⅛ to ¼ inch long for best results. Compositions containing from about one-fourth to one-half percent polyester or nylon fibers, the fibers being about ¼ inch in length on the average, are preferred.

The fibers that are added to the compositions of this invention can be from about 1½ to 15 denier per filament, with filaments of the lower denier values being preferred. The most preferred fiber-containing compositions of this invention also contain up to about 1% of silicone oil.

DETAILS OF THE INVENTION

The copolyester compositions of the present invention are condensation polymers containing in polymerized form a polymethylene glycol, an aliphatic dicarboxylic acid and isophthalic acid. In the copolyester compositions of this invention, the ester linkages are an integral part of the polymer chain.

The polymethylene glycols, HO—$(CH_2)_n$—OH, useful in the copolyester of the invention are typically ethylene glycol, trimethylene glycol, tetramethylene glycol, pentamethylene glycol and hexamethylene glycol. The preferred polymethylene glycol is ethylene glycol ($n=2$) because of the desirable properties of the copolyester produced therefrom. Mixtures of polymethylene glycols can also be used.

Representative aliphatic dicarboxylic acids, HOOC—$(CH_2)_x$—COOH, include glutaric, HOOC—$(CH_2)_3$—COOH; adipic, HOOC—$(CH_2)_4$—COOH; pimelic, HOOC—$(CH_2)_5$—COOH; suberic, HOOC—$(CH_2)_6$—COOH; azelaic, HOOC—$(CH_2)_7$—COOH; and sebacic, HOOC—$(CH_2)_8$—COOH. Preferred is adipic acid. Mixtures of aliphatic dicarboxylic acids can be used.

The relative amounts of the aliphatic acid and the isophthalic acid are important since if too much of either one is used, the copolyester tends to be too crystalline, too high-melting or too rigid. High crystallinity and high polymer melt temperature are undesirable for compositions that are to be inserted into the ear canal, the desirable properties being plasticity and pliability at ordinary temperatures. Therefore, it is necessary that isophthalic acid comprise at least 10 mol percent and not over 50 mol percent of the total acid component of the copolyester, and preferably from about 20 to 30 mol percent thereof. A portion of isophthalic acid can be replaced with other aromatic dicarboxylic acids such as phthalic acid or terephthalic acid provided that the isophthalic acid comprises at least 85% of the total weight of the aromatic acid.

The copolyesters of the present invention can be prepared by any of the methods known in the art for the preparation of polyesters. A convenient and useful method is melt polymerization wherein the polymethylene glycol and the mixture of dicarboxylic acids are heated together in the molten state. The acid components of the copolyester can be introduced as a mixture of acids, mixture of acid and lower alkyl diester, mixture of lower alkyl diesters of the acid, or as a mixture of bis(hydroxyalkylene)esters.

When lower alkyl diester is used, it is preferably a dimethyl ester since the alcohol formed during the transesterification step is most readily removed when the alcohol formed is methanol. Generally, a slight excess of polymethylene glycol is used and the transesterification reaction is carried out at about 120° to 250°C. until methanol evolution ceases. The pressure is usually then reduced and the temperature is increased to about 250° to 280°C. and the conditions are maintained until the copolyester of desired intrinsic viscosity is obtained.

The desired ratio of the acid components of the copolyester is determined by the initial reactant ratio of the acid or the acid derivatives, particularly when the copolyester is prepared in the presence of a slight excess of polymethylene glycol. If desired, suitable catalysts known in the art to catalyze transesterification and polyester condensation reaction such as oxides of lead, oxides of antimony, and acetates of cobalt, zinc, lead, manganese, cadmium and the like can be used.

The invention copolyesters also can be prepared by the condensation of the corresponding acid halides with the polymethylene glycols. Thus, a mixture of isophthaloyl chloride and adipoyl chloride can be reacted with ethylene glycol to provide poly(ethylene isophthalate/adipate).

Concerning the extremely low crystallinity of the compositions of this invention as determined by X-ray diffraction, it is noted that such low crystallinity persists even through drawing and heating operations that are sometimes employed to induce crystallinity in art-known copolyesters.

The copolyester compositions of this invention have an intrinsic viscosity in the range of about 0.30 to 0.80, preferably in the range of 0.45 to 0.55. Intrinsic viscosity is defined by the formula $$\text{limit} \frac{\ln \eta r}{C} \text{ as } C \text{ approaches } 0$$

wherein $\eta r$ is the viscosity of a dilute solution of the copolyester in a solvent mixture of 25 volume percent trifluoroacetic acid and 75 volume percent methylene chloride divided by the viscosity of the solvent in the same units and at the same temperature and C is the concentration in grams of polymer per 100 cc of the solution.

The degree of polymerization of the copolyesters as indicated by the defined intrinsic viscosity range, and the utilization of the aliphatic dicarboxylic acid and isophthalic acid in the defined proportion provide copolyesters which have a polymer melt temperature of from about 20°C. to 45°C. Polymer melt temperature is defined as the temperature at which the polymer becomes molten and moldable, and is determined by moving a polymer sample across a metal bar having a temperature gradient between the ends of the bar and noting the temperature zone at which the polymer sample leaves a trail. Polymer melt temperature is generally recognized in the art as the minimum temperature at which heat processing of the polymer, such as molding, melt spinning and the like, can be carried out readily.

The invention copolyester compositions are characterized by a unique combination of properties which make them particularly useful for earplug use. The novel copolyester compositions provide advantages not possessed by any single composition previously suggested in the art as earplug material. Furthermore, they do not depend upon solvents for plasticity nor upon curing agents and subsequent curing for dimensional stability.

The combination of intrinsic viscosity, particular aromatic dicarboxylic acid and the proportion of aromatic dicarboxylic acid to aliphatic dicarboxylic acid as defined provides copolyester compositions that are readily moldable and suitably thermoplastic in the temperature range of about 20°C. to 45°C. The compositions can, therefore, be inserted into the ear canal and molded to readily conform to the irregular contour of the ear canal at ambient temperatures.

The compositions are sufficiently soft and resilient so that the earplugs can be worn for an extended period without discomfort. The composition does not become hard on standing. Because of the slight surface tackiness of the composition, an effective seal between the earplug and the wall of the ear canal is maintained. When desired, the entire plug can be removed readily without leaving small particles of the copolyester composition adhering to the wall of the ear canal because the cohesive force of these compositions is greater than the adhesive force. The invention copolyester compositions can be used repeatedly, each insertion resulting in custom-fitting of the earplug. When the earplug has acquired an amount of wax and/or dirt to become objectionable, it can be discarded and inexpensively replaced.

The copolyester compositions are clear compositions but delustering additives such as titanium dioxide can be incorporated to make them opaque if desired. For further cosmetic purposes such as matching the color of skin, pigments and/or dyes can also be incorporated.

Custom-fitted earplugs are readily fabricated using the copolyester compositions of the invention. For example, a mass of the material is shaped into an approximately conical or frustum-shaped piece and is gently pressed into the ear canal. By gently pressing in several directions, the plug can be made to readily conform to the contour of the ear canal. The amount of the polyester composition needed will depend upon the particular type of earplug desired. When only the ear canal and the concha of the ear are to be filled normally from about 2 to 4 cubic centimeters of the copolyester composition is used, whereas when the auditory canal and the whole pinna of the ear are to be filled, from about 5 to 15 cubic centimeters is used.

While the utility of the invention copolyesters has been described in terms of earplug applications, it will be clear to those skilled in the art that the compositions will be useful in other areas that make use of their characterizing properties.

The following Examples are meant to illustrate but not to limit this invention.

EXAMPLE 1

Dimethyl isophthalate, 1.75 kg, and ethylene glycol, 1.18 kg, were charged into a reactor. A mixture of 2.05 g manganese acetate and 1.35 g. diantimony trioxide ester exchange catalyst was added. The mixture was heated with agitation at atmospheric pressure to 240°C., during which methanol and some ethylene glycol were distilled out. The reaction mixture was kept at 240°C. until the ester exchange reaction was completed, indicated by the cessation of methanol evolution. To the reaction vessel, 2.8 kg of bis(hydroxyethyl)adipate was added. The pressure of the vessel was reduced to about 1 mm Hg over a period of about 45 minutes and the reaction temperature was increased to 260°C., and kept at 260°C. for 5 hours. After some cooling and restoration of the pressure to atmosphere, the product was removed from the reaction vessel by extruding. The product copolyester was a poly(ethylene isophthalate/adipate) having a mol ratio of isophthalate to adipate of 43 to 57 and an intrinsic viscosity of 0.41, as determined in a solvent mixture of 25% by volume of trifluoroacetic acid and 75% by volume of methylene chloride.

EXAMPLE 2

A copolyester having the same mol ratio of isophthalate to adipate as in Example 1 but having an intrinsic viscosity of 0.77 was provided by repeating the preparation substantially as described in Example 1 except that the reaction mass was kept at 270°C. for 5½ hours.

EXAMPLE 3

Dimethyl isophthalate, 1.37 kg, and ethylene glycol, 0.92 kg, were charged into a reactor together with an ester exchange catalyst which was a mixture of 2.05 g manganese acetate and 1.35 g diantimony trixoide. The ester exchange reaction was carried out as described in Example 1, and 3.29 kg of bis(hydroxyethyl)adipate was added to the product thus obtained. The polymerization was carried out at 265°C. at 1 mm Hg pressure for 6 hours to provide a poly(ethylene isophthalate/adiphate) having a mol ratio of isophthalate to adipate of 33 to 67 and having an intrinsic viscosity of 0.56, as determined in a solvent mixture of 25 volume percent trifluoroacetic acid and 75 volume percent methylene chloride.

EXAMPLE 4

Using the reactants and the procedure of Example 3, except for the use of 0.91 Kg. of dimethyl isophthalate, poly(ethylene isophthalate/adipate) was prepared having a mol ratio of isophthalate to adipate of 25 to 75 and having an intrinsic viscosity of 0.71. The copolyester was found to have acceptable tackiness and stiffness for earplug use.

EXAMPLE 5

To 100 gms of the copolyester of Example 4, 1.0 gram of silicone oil, dimethylpolysiloxane fluid, (DC-200, Dow-Corning) and 0.5 gm "Dacron" polyester fiber of 1½ denier per filament and ¼ inch in length were added and mixed to provide a composition of decreased tackiness and increased stiffness over that prepared as in Example 4. The copolyester with these additions had acceptable tackiness and stiffness for earplug use.

EXAMPLE 6 (Utility)

The utility of the invention copolyester in an earplug application for attenuation of sound was demonstrated in the threshold of hearing test using an automatic audiometer (Model ARJ-4, Rudmose Associates, Richardson, Texas) in a sound booth (Model 400-A. Industrial Acoustics Co., New York, N. Y.). The threshold of hearing was determined on a subject with no ear protection over the sound frequencies of 500 to 6,000 cycles per second. Similar thresholds of hearing were determined with (1) earplugs fabricated in place from a commercial wax-type composition, and (2) earplugs fabricated in place from the copolyester of Example 1. The attenuation in decibels of the various frequencies relative to the threshold hearing with no earplugs was determined. The average attenuation for the right and left ears are given in the following Table. The results show the copolyester composition of the invention provides superior sound attenuation.

TABLE

| Sound Frequencies (Cycles per Second) | Average Attenuation (decibels) | |
|---|---|---|
| | Copolyester Example 1 | Commercial Wax-Type |
| 500 | 21 | 11 |
| 1,000 | 25 | 17 |
| 2,000 | 42 | 28 |
| 3,000 | 36 | 24 |
| 4,000 | 43 | 21 |
| 6,000 | 48 | 21 |

I claim:
1. A composition suitable for use as a human earplug, the composition comprising
  A. a linear copolyester consisting essentially of, in polymerized form,
    1. at least one polymethylene glycol of the formula HO—$(CH_2)_n$—OH, wherein $n$ is an integer of 2 to 6,
    2. at least one aliphatic dicarboxylic acid of the formula HOOC—$(CH_2)_x$—COOH, wherein $x$ is an integer of 3 to 8, and
    3. about 10 to 50 mol percent of the total amount of acid in the copolyester of isophthalic acid;
  the copolyester having
    4. an intrinsic viscosity of about 0.3 to 0.8,
    5. a degree of crystallinity less than about 10%, as determined by X-ray diffraction, and
    6. a polymer melt temperature of 20°C to 45°C;
  B. up to 1% of a silicone oil; and
  C. up to 1% of fibers.
2. The composition of claim 1 wherein the isophthalic acid in (A) (3) comprises from about 20 to 30 mol percent of the total amount of acid in the copolyester.
3. The composition of claim 1 in which the copolyester has an intrinsic viscosity of about 0.45 to 0.55.
4. The composition of claim 1 wherein the glycol in (A) (1) is ethylene glycol.
5. The composition of claim 1 wherein the acid in (A) (2) is adipic acid.
6. The composition of claim 1 wherein the glycol in (A) (1) is ethylene glycol, the acid in (A) (2) is adipic acid and the isophthalic acid in (A) (3) comprises about 20 to 30 mol percent of the total amount of acid in the copolyester.
7. The composition of claim 1 wherein the fibers in (C) are fibers of nylon or polyester ⅛ inch to ¼ inch long.
8. The composition of claim 6 wherein the fibers in (C) are fibers of nylon or polyester ⅛ to ¼ inch long.

* * * * *